(12) United States Patent
O'Hare et al.

(10) Patent No.: US 8,911,149 B2
(45) Date of Patent: Dec. 16, 2014

(54) X-RAY COMPUTED TOMOGRAPHY DEVICE CALIBRATION AND VERIFICATION APPARATUS

(71) Applicant: Hexagon Metrology, Inc., North Kingstown, RI (US)

(72) Inventors: Jonathan J. O'Hare, Warwick, RI (US); Stephen Darrouzet, West Warwick, RI (US)

(73) Assignee: Hexagon Metrology, Inc., North Kingstown, RI (US)

( * ) Notice: Subject to any disclaimer, the term of this patent is extended or adjusted under 35 U.S.C. 154(b) by 0 days.

(21) Appl. No.: 14/281,006

(22) Filed: May 19, 2014

(65) Prior Publication Data

US 2014/0254770 A1  Sep. 11, 2014

Related U.S. Application Data

(63) Continuation of application No. 13/752,698, filed on Jan. 29, 2013, now Pat. No. 8,764,290.

(60) Provisional application No. 61/592,169, filed on Jan. 30, 2012.

(51) Int. Cl.
*G01D 18/00* (2006.01)
*G01T 7/00* (2006.01)

(52) U.S. Cl.
CPC .................................... *G01T 7/005* (2013.01)
USPC .............................................. 378/207; 378/18

(58) Field of Classification Search
USPC ................................................ 378/4–20, 207
See application file for complete search history.

(56) References Cited

U.S. PATENT DOCUMENTS 6,364,529 B1 *  4/2002  Dawson ........................ 378/207
8,777,485 B2 *  7/2014  Holt .............................. 378/207

* cited by examiner

*Primary Examiner* — Hoon Song
(74) *Attorney, Agent, or Firm* — Sunstein Kann Murphy & Timbers LLP

(57) ABSTRACT

An apparatus for calibrating an x-ray computed tomography device has a plurality of objects formed from a material that is visible to x-rays, and a base at least in part fixedly supporting the plurality of objects so that each of the plurality of objects contacts at least one of the other objects. Each one of the plurality of objects: 1) is configured to receive x-rays without changing shape, 2) has substantially the same shape and size as the other objects, 3) has an attenuation value to x-rays ("object attenuation value"), and 4) is symmetrically shaped relative to its center point. Like the objects, the base also has an attenuation value to x-rays (the "base attenuation value"). The object attenuation value is greater than the base attenuation. Each of the plurality of objects is kinematically locked in place on the base.

20 Claims, 6 Drawing Sheets

X-RAY COMPUTED TOMOGRAPHY DEVICE CALIBRATION AND VERIFICATION APPARATUS

PRIORITY

This patent application is a continuation of U.S. patent application Ser. No. 13/752,698, filed Jan. 29, 2013, entitled, "X-RAY COMPUTED TOMOGRAPHY DEVICE CALIBRATION AND VERIFICATION APPARATUS," and naming Jonathan J. O'Hare and Steven Darrouzet as inventors, the disclosure of which is incorporated herein, in its entirety, by reference, which claims priority from provisional U.S. patent application Ser. No. 61/592,169, filed Jan. 30, 2012, entitled, "X-RAY COMPUTED TOMOGRAPHY DEVICE CALIBRATION AND VERIFICATION APPARATUS," and naming Jonathan J. O'Hare and Stephen Darrouzet as inventors, the disclosure of which is incorporated herein, in its entirety, by reference.

FIELD OF THE INVENTION

The invention generally relates to calibration devices and, more particularly, the invention relates to calibration of x-ray computed tomography devices/CT machines.

BACKGROUND OF THE INVENTION

Coordinate measuring machines (CMMs) are the gold standard for accurately measuring a wide variety of different types of work pieces. For example, CMMs can measure critical dimensions of aircraft engine components, surgical tools, and gun barrels. Precise and accurate measurements help ensure that their underlying systems, such as an aircraft in the case of aircraft components, operate as specified.

Inaccurate measurements can have catastrophic effects. Accordingly, to ensure that CMMs deliver accurate measurements, the CMM industry has developed well-defined accuracy verification standards, procedures, and gauging tools to calibrate and verify the underlying machines taking these measurements. To those ends, a CMM verification procedure typically requires hard gauges that are traceable for uncertainty calculations, and designed in such a way to ensure that they (i.e., the gauges) are dimensionally stable.

More recently, those in the art have begun using computed tomography (CT) systems as CMMs for coordinate metrology. Undesirably, however, such CT systems known to the inventors lack both well-defined verification standards, as well as gauging tools designed for that purpose.

SUMMARY OF THE INVENTION

In accordance with one aspect of the invention, an apparatus for calibrating an x-ray computed tomography imaging device (e.g., a CT device) has a plurality of objects formed from a material that is visible to x-rays, and a base at least in part fixedly supporting the plurality of objects so that each of the plurality of objects contacts at least one of the other objects. Each one of the plurality of objects: 1) is configured to receive x-rays without changing shape, 2) has substantially the same shape and size as the other objects, 3) has an attenuation value to x-rays ("object attenuation value"), and 4) is symmetrically shaped relative to its center point. Like the objects, the base also has an attenuation value to x-rays (the "base attenuation value"). The object attenuation value is greater than the base attenuation. Each of the plurality of objects is kinematically constrained on the base.

Among other things, each of the plurality of objects may include ruby material, and the base may include ceramic. Moreover, the apparatus also may have a securing member normally applying a force to the plurality of objects. The securing member cooperates with the base to fixedly secure the plurality of objects to be substantially unmovable, or at least minimally constrained.

In preferred embodiments, the plurality of objects all have a substantially precise spherical shape, the same precise diameter/size, and a low coefficient of thermal expansion (e.g., lower than that of steel). Moreover, to ensure accurate measurements, the plurality of objects may be oriented in a straight line such that the cumulative distance of the plurality of objects may be known directly from the sum of their diameters/sizes.

To more effectively stabilize the objects, each object may be kinematically locked without any external locking components between the objects. This also precludes use of bonding agents, such as epoxy or glue (which may interfere with imaging), between the objects. For example, each object may be minimally constrained with no more than four contact points with other objects and the base. In illustrative embodiments, this kinematic locking ensures that the centers of the objects all form a straight line that has no error/deviation of greater than about 1 micron. In alternative embodiments, this error/deviation may exceed about 1 micron—for example, it may be about 1.5 microns, about 2 microns, or about 3 microns. Each larger error, however, results in greater uncertainty for determining the distances between the objects, thus sacrificing accuracy. Accordingly, those skilled in the art can select an appropriate deviation based upon the accuracy required for the underlying application/machine being calibrated.

To contain the objects in this manner, the base may have a groove with substantially straight and flat surfaces. For example, the groove may form a V-shape having an angle of between about 60 and 120 degrees. In addition, each of the plurality of objects may have the same maximum dimension (e.g., a diameter if the object is spherically shaped) of no greater than about 10 millimeters. For example, the maximum dimension of the object may be about 1 millimeter, and could be as 0.1 millimeters or smaller.

The plurality of objects may be ground or lapped objects, and/or may include a third-party certification of at least one of its dimensional properties. Moreover, each of the plurality of objects preferably is a free-standing object (e.g., separate spherically shaped, independent, unconnected objects). Some embodiments use three or more objects.

In accordance with another embodiment of the invention, a method of calibrating or verifying the dimensional accuracy of an x-ray computed tomography machine provides an x-ray computed tomography machine having calibration settings, and uses the x-ray machine to image a gauge to produce a gauge reconstruction (a 3D reconstruction of the gauge). The gauge has a base at least in part supporting three or more objects, where each of the plurality of objects has substantially the same shape and size and is kinematically secured on the base. Each of the objects has a center, and the distance between the centers of each object is known ("known center distance values"). The method then measures, in the reconstructed three-dimensional volume or derived surface of the gauge ("gauge reconstruction"), the distance between at least two pairs of objects to produce measured center distance values, compares the measured center distance values against the known center distance values, and uses the comparison to determine if there is a distance error in the gauge reconstruction.

The method then may modify the calibration settings of the x-ray computed tomography machine if the comparison determines that there is a distance error in the gauge reconstruction. Moreover, to produce the gauge reconstruction, the method may produce a plurality of gauge reconstructions from a plurality of different projections, and form a three dimensional model of the gauge using the plurality of projections. The method then may measure the three dimensional model of the gauge.

In accordance with another embodiment, an apparatus for calibrating an x-ray computed tomography device has at least three objects formed from a material that is visible to x-rays. Each of the at least three objects 1) is configured to receive x-rays without changing shape, 2) have an object attenuation value to x-rays, and 3) have an identifiable region. The apparatus also has a base at least in part fixedly supporting the objects so that each object contacts at least one of the other objects. The base has a base attenuation value to x-rays, and the identifiable regions of the at least three objects form a substantially straight line on the base. The object attenuation value is greater than the base attenuation value, and each of the objects is locked in place on the base in a manner that prevents object translational movement.

The at least three objects may be free standing objects and locked in place on the base in a manner that permits the objects to rotate relative to the base. The objects each may have a precision to at least 0.01 millimeters (e.g., they may have a precision to 0.0001 millimeters). Moreover, the at least three objects each may be symmetrically shaped relative to a center point and, in that case, the identifiable region of each object may be that center point.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

DESCRIPTION OF ILLUSTRATIVE EMBODIMENTS

In illustrative embodiments, an apparatus for calibrating (or verifying) an x-ray computed tomography machine provides fine pitch details to enable more accurate measurements of a work piece—particularly, more accurate measurements of smaller dimensions of a work piece (e.g., in the sub-millimeter level, such as to the micrometer or nanometer level). To that end, the apparatus has a base that supports a plurality of objects by kinematically locking them into place along an interior detail or groove. Details of illustrative embodiments are discussed below.

Figure 1A:
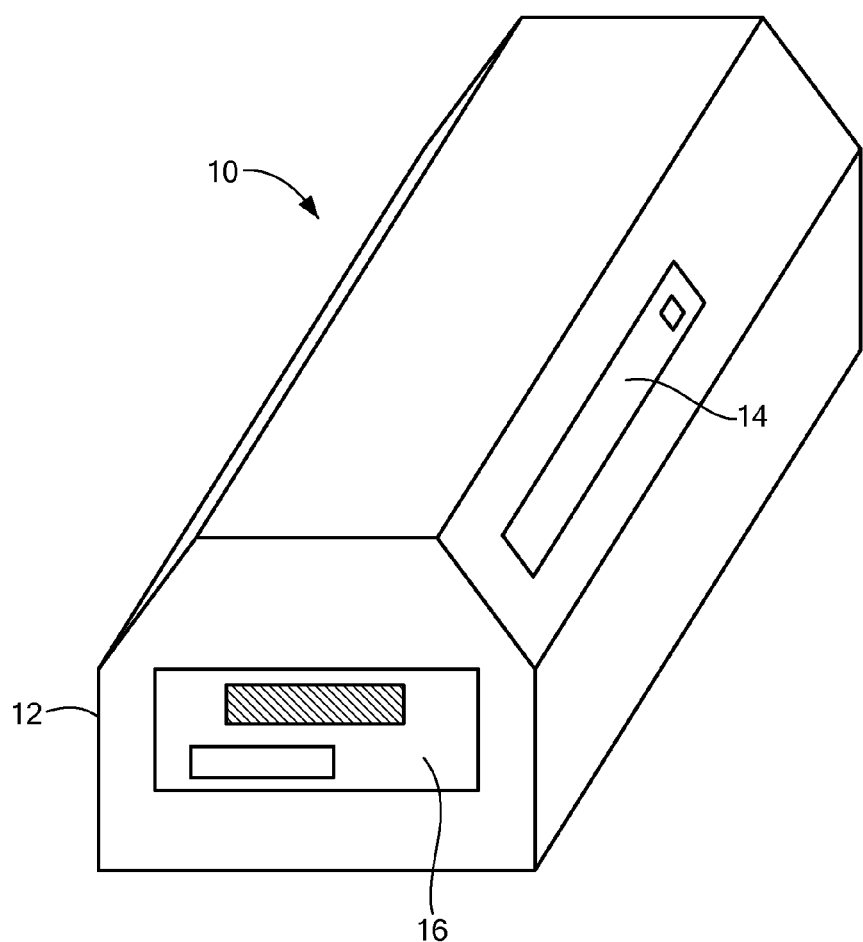
FIG. 1A schematically shows an x-ray computed tomography device that may use illustrative embodiments of the invention.
Figure 1B:
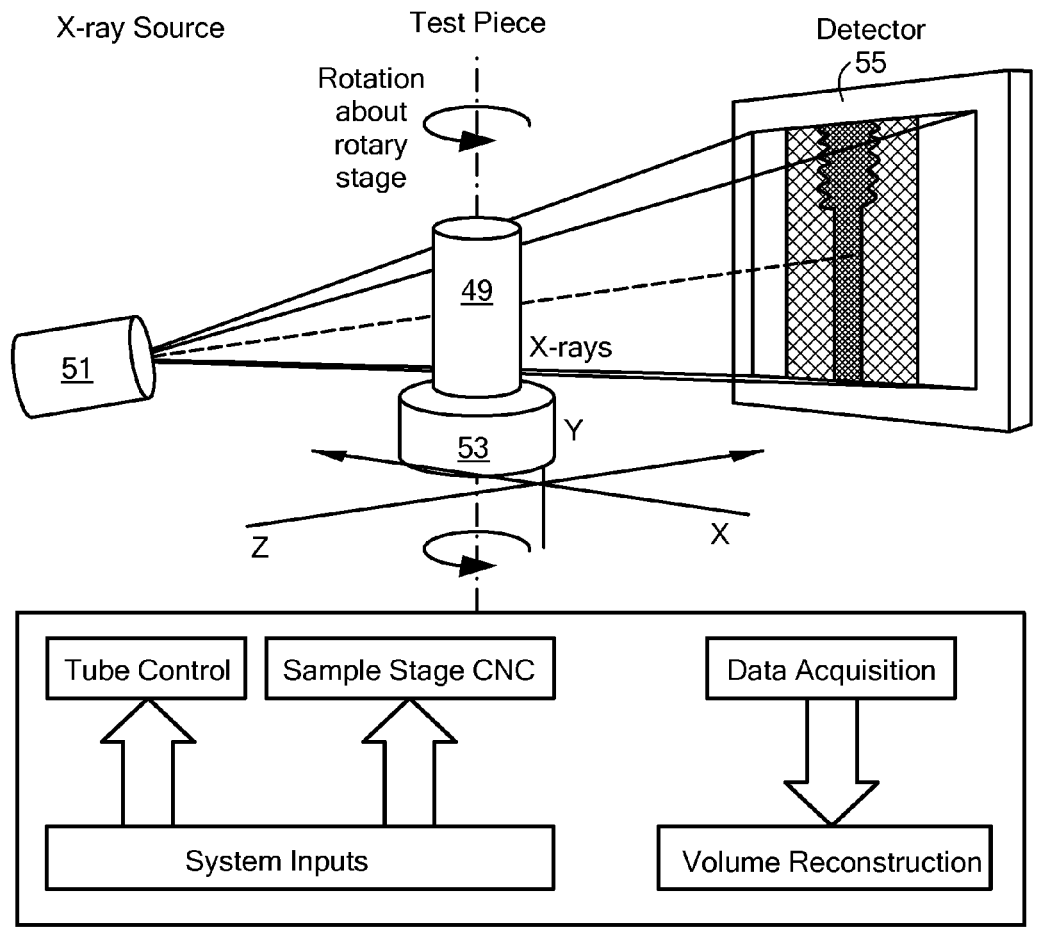
FIG. 1B schematically shows internal components of the device of FIG. 1A.

FIGS. 1A and 1B schematically show an x-ray machine/computer tomography device 10 that may use a calibration gauge configured in accordance with illustrative embodiments. It should be noted that although this discussion primarily relates to calibration, principles of various embodiments apply to verification of the accuracy of x-ray computed tomography machines 10. Accordingly, discussion of calibration is not intended to limit all embodiments of the invention.

Among other things, the x-ray computed tomography 10 may be a computed tomography system (a/k/a a "CT system" or a CT machine) that produces a three dimensional model of a work piece within its interior (referred to as a "work piece reconstruction"). To those ends, the x-ray computed tomography machine 10 has a housing 12 forming an interior chamber for containing, among other things (see FIG. 1B), 1) a work piece 49 to be measured, 2) an x-ray gun 51 for generating x-rays, 3) a rotary stage 53 for rotating the work piece 49, and 4) a detector 55 for detecting the image of the work piece after it is imaged by the x-ray gun 51. An access door 14, which may be made from a transparent material, provides access to the interior for adding and removing work pieces. For example, the work piece may be a cardiovascular stent commonly used in coronary angioplasty procedures. A control panel 16 on the side of the machine 10 acts as the control interface for an operator.

To produce the 3D model_of the work piece (the "reconstruction"), the CT system moves the work piece relative to the x-ray guns 51. For example, the CT system may rotate the work piece a full 360 degrees on the rotary stage 53, and take multiple x-ray images (known in the art as "projections" or "projection angles") of the work piece during rotation. During and/or after rotating the work piece, a model building module (e.g., post-processing software executing on a local microprocessor or microcontroller) converts the data of all the projections into a 3D model of the work piece—the noted reconstruction. It is this 3D model—which may be a software model—that may be measured to confirm the work piece's dimensional accuracy. Thus, if the work piece is a small medical device, such as a cardiovascular stent, then measurement software may precisely measure selected features of the stent, such as its radius, wall thickness, etc. . . . .

If the CT system is not properly calibrated, however, then these work piece measurements likely will be inaccurate. Accordingly, the operator or other person should calibrate the CT system prior to use. Undesirably, however, the inventors know of no highly reliable and fine pitch mechanism or technique to calibrate conventional CT systems to fine pitch details. The inventors thus have developed a highly accurate, fine pitch calibration gauge that fills this deficiency in the art.

Figure 2:
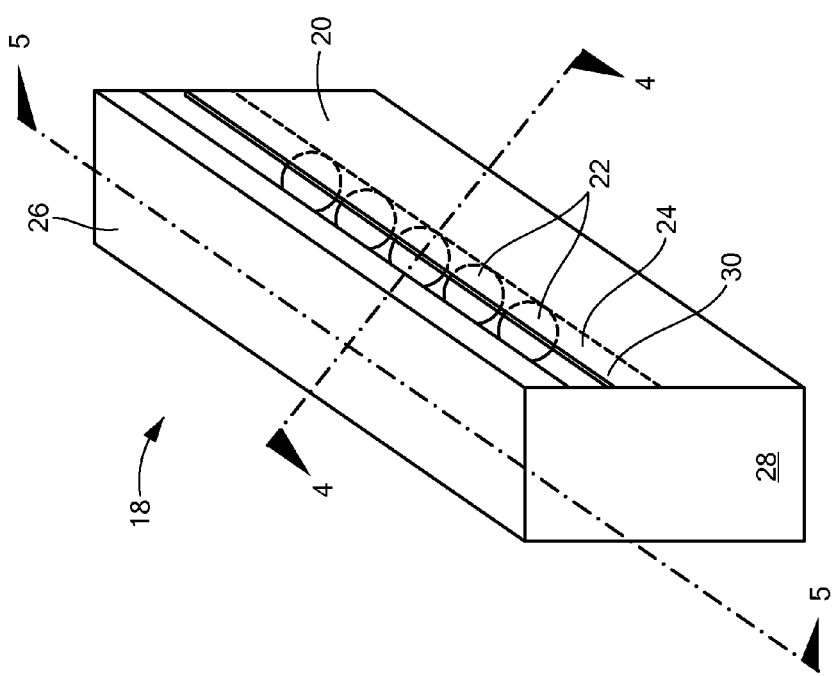
FIG. 2 schematically shows an x-ray calibration and verification gauge configured in accordance with illustrative embodiments of the invention.

Specifically, FIG. 2 schematically shows an illustrative gauge 18 for calibrating or verifying a CT machine 10. The gauge 18 has a base 20 that supports a plurality of discrete objects 22 that act as guideposts in the calibration process. More specifically, in illustrative embodiments, the objects 22 comprise three or more spheres (also identified by reference number "22") that are ground or lapped to have very precise qualities (precise symmetry, shape, size, volumes, centers, geometry, etc . . . ). In illustrative embodiments, the spheres 22 are certified by some reliable and well-known third party to have certain measurement qualities. The spheres 22 are free-standing and independent structures—they are not integral to or even connected to each other. Instead, the spheres 22 merely contact each other on the base 20. As discussed in greater details below, some embodiments position the spheres 22 so that their centers form a straight line.

As noted above and discussed in greater detail below, the base 20 kinematically locks the spheres 22 into place along an interior detail or accurately formed groove 24. In particular, the spheres 22 are constrained so that they cannot move translationally relative to the base 20—i.e., in a direction relative to the X-axis, Y-axis, or Z-axis of the base 20. Some embodiments also are constrained so that the spheres 22 cannot move in any other manner, e.g., they cannot rotate relative to the base 20. Other embodiments, however, may permit non-translational motion, such as rotation relative to the base 20. In either case, the gauge 18 simply uses point or region contact to retain the spheres 22 within the base 20. The gauge 18 thus does not require additional securing components, adhesive, or features to keep the spheres 22 in their appropriate positions.

To that end, to ensure that the spheres 22 remain on the base 20, the gauge 18 also has a securing member 26 secured to the base 20 to normally apply a downward bias force to the spheres 22. For example, the bottom surface of the securing member 26 may have a soft material layer 27 (e.g., foam) to provide a minimal, downwardly applied force (i.e., a "preload") to the spheres 22. This ensures that the spheres 22 remain in place, thus maintaining measurement fidelity. Other embodiments do not have the soft material layer 27. In that case, the securing member 26 illustratively makes contact with a very small region of each sphere 22. Ideally, that small region is a point. Even the embodiment using the material layer 27, which may contact a relatively large region of the spheres 22, still effectively produces a force vector in a direction through the center of each sphere 22 and toward the longitudinal axis of the base 20.

Each end of the gauge 18 also may have an end cap 28 that both secures the base 20 to the securing member 26, and precisely positions the spheres 22 within the gauge interior. Accordingly, in illustrative embodiments, at least some of the following elements use point contact to kinematically lock the spheres 22 in place: the end caps 28, securing member 26, groove of the base 20, and the spheres 22 themselves.

To calibrate the CT system, a calibration module measures the distance between some identifiable regions of the objects. For example, in the sphere embodiment, the calibration module may measure between the centers of the one or more of the spheres 22. If the object was not in the form of a sphere (e.g., in the form of a protrusion, cube, cylinder, irregular shape, etc . . . ), then the identifiable region could be the center or some other area, such as an end, a discontinuity, a corner, the intersection of two portions, etc. . . . Even if the objects 22 are spheres, the identifiable portion could be an outside region.

Accordingly, it is most important for the spheres 22 to be visible on the x-ray images. To that end, the spheres 22 preferably are formed from a material having a higher attenuation to x-rays than the attenuation of the base 20. For example, the spheres 22 may be formed from ruby, sapphire, or other material for the purpose of providing low thermal expansion and x-ray attenuation near the middle of the CT system's range of intensity values. The base 20 may be formed from a ceramic material with a high stiffness and a low thermal expansion, but with an x-ray attenuation that is relatively low when compared to the material of the spheres 22. This differential in attenuations should provide good contrast and a clear separation between the surfaces of interest (i.e., the spheres 22) and the base 20. Those in the art should understand that the base 20 may be formed from another material having similar properties.

In illustrative embodiments, the coefficient of thermal expansion of the spheres 22 and base 20 is as low as possible, such as no greater than that for steel. Another important consideration of the base 20 is for it to be in a specified form for the purpose of accurately supporting three or more spheres 22 in a precisely straight line while in contact with each other. As noted herein, this line should be straight within a predefined error, such as 1 micron.

Figure 3:
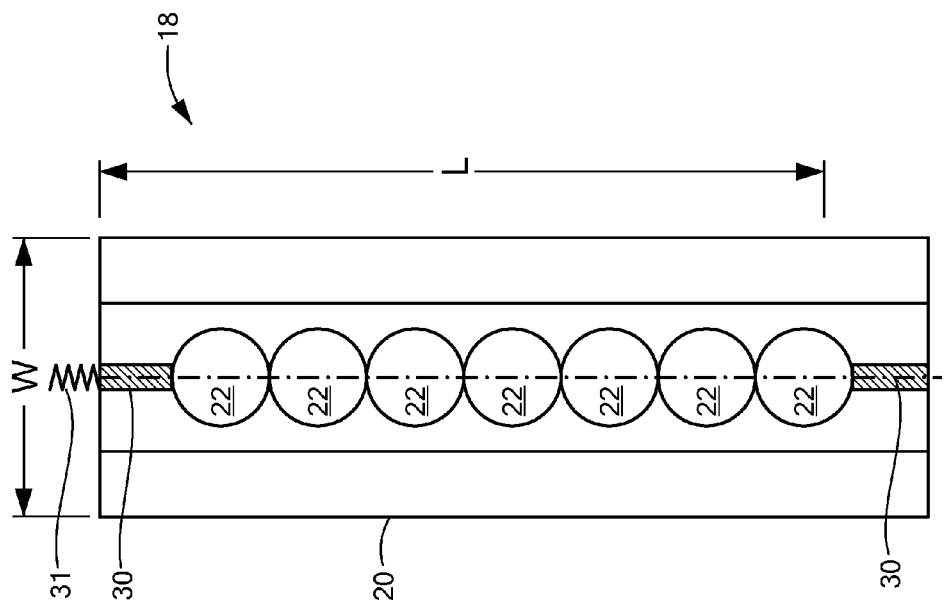
FIG. 3 schematically shows a plan view of the gauge of FIG. 2 with its top portion removed to show the internal spheres.

FIGS. 3, 4A, 4B, and 5 all show more details of the complete gauge 18. Specifically, FIG. 3 schematically shows a plan view of the gauge 18 with its securing member 26 removed. It should be noted that some embodiments do not have a securing member 26 and simply position the spheres 22 on the base 20 without being constrained at their tops. In this case, as free standing structures, the spheres 22 are fixed during imaging, although they may move before imaging. This view of FIG. 3 shows the spheres 22 lined up in a substantially straight line along a groove 24 within the base 20. As shown, there are no spaces between the spheres 22—they ideally have a point contact that in part kinematically locks the spheres 22 in place on the base 20. This view also shows a pair of optional spacers 30 protruding from the end cap 28. In some embodiments, one spacer 30 is fixed to provide a hard stop, while the other spacer 30 is connected with a spring 31 to provide a soft stop and a minimal applied force that ensures contact of all the spheres 22. Some embodiments use spacers 30 that both provide a hard stop, with or without point contact. Other embodiments have spacers 30 that both use springs 31.

Figure 4A:
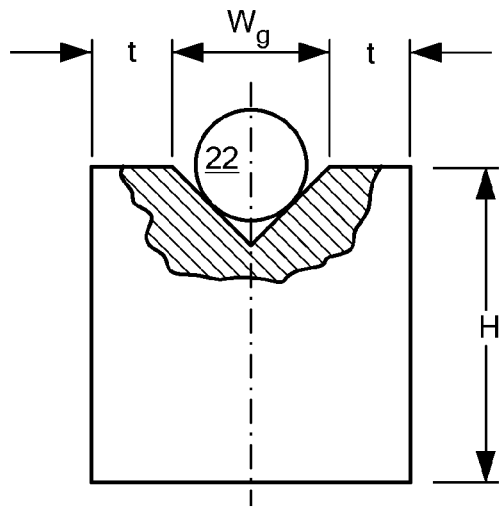
FIG. 4A schematically shows a cross sectional view of the gauge of FIG. 2 along cross-line 4-4
Figure 4B:
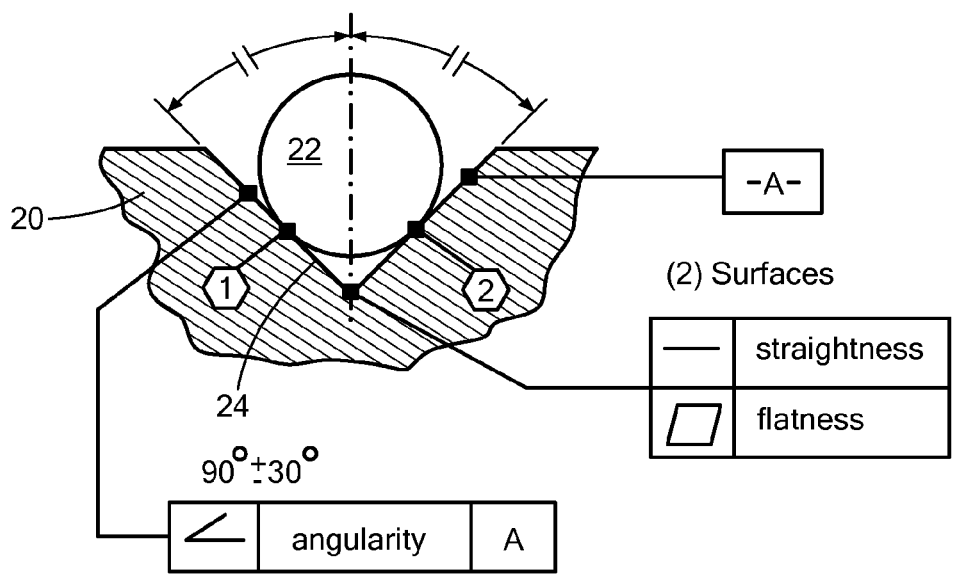
FIG. 4B schematically shows an enlarged and simplified view of the view shown in FIG. 4A.
Figure 5:
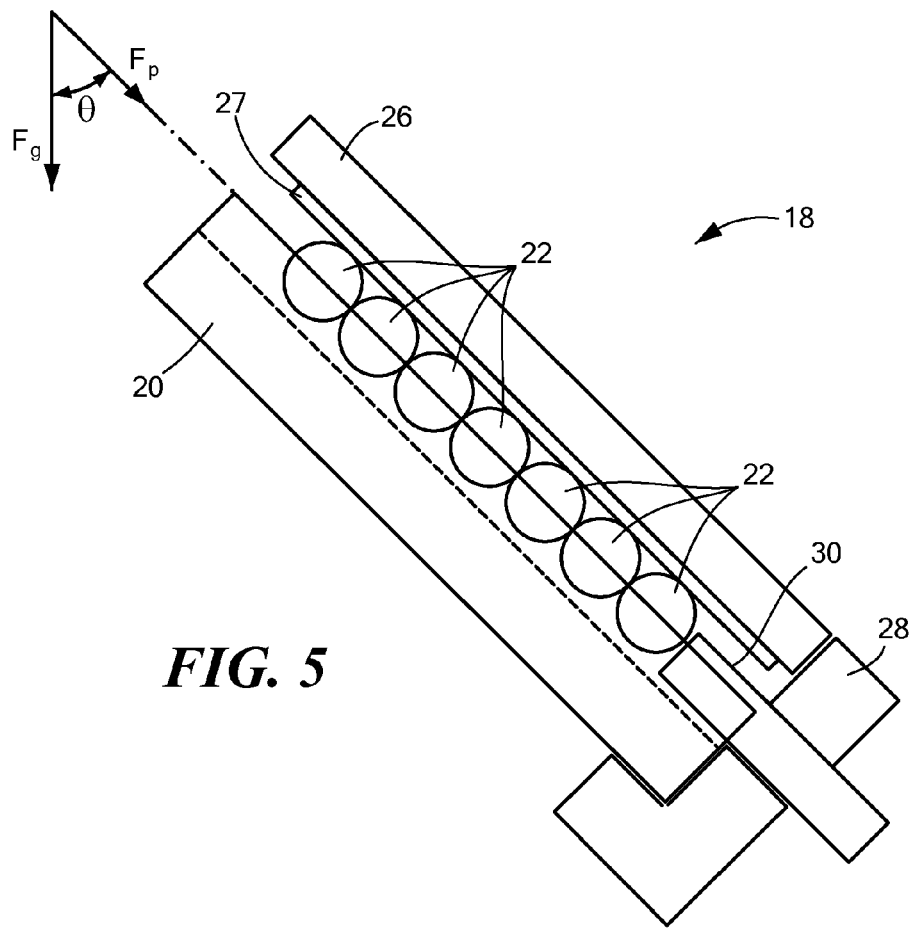
FIG. 5 schematically shows a longitudinal cross-sectional view of the gauge of FIG. 2 along cross-line 5-5.

To line up in a substantially straight line, the surfaces of the spheres 22 and groove 24 should be precisely configured. Specifically, as shown in FIGS. 4A and 4B, the groove surfaces should be very planar, smooth, and straight. The angle formed by the groove 24 can be selected by the designer to ensure accuracy. For example, the groove 24 may, in some implementations, form an angle of between about 60 and 120 degrees.

FIG. 4B best shows the kinematic locking of the spheres 22. Specifically, as suggested above, in the ideal case, each sphere 22 only contacts the groove 24 at two infinitesimally small, discrete points. In fact, in illustrative embodiments, those two points of groove contact effectively form a single force vector in a direction that is normal to the longitudinal axis of the base 20. In a corresponding manner, each sphere 22 (ideally) only contacts each neighboring sphere 22 at one infinitesimally small point—providing a force vector along the longitudinal axis of the base 20. This ensures that the spheres 22 are minimally constrained, thus providing maximum stability. In more simplified terms, if it is minimally constrained, then a sphere 22 should not rock or move—it is substantially immovable during normal operation (absent application of an unusual force). Indeed, in actual use, the spheres 22 cannot contact at infinitesimally small points.

Those skilled in the art should drive toward that end, however, by using the more finely and accurately produced spheres 22. The spheres 22 thus may be formed to have a very fine precision. For example, the spheres 22 have a diameter with a precision to at least 0.01 millimeters. Specifically, as used herein, a precision of at least 0.01 millimeters may have an even finer precision, such as 0.001 millimeters, 0.005 millimeters, 0.0001 millimeter, 0.00001 millimeters, etc. . . . As another example, the spheres 22 may have a diameter of 10.0001 millimeters, within some known tolerance, such as 0.00005 millimeters. All spheres 22 of the same gauge 18 may be the same size, or different. In either case, the diameters of the spheres 22 are known to the precision noted. Accordingly, illustrative embodiments can detect a variance of the reading by the CT machine 10 by an amount on the order of the precision of the sphere 22—down to the micrometer or nanometer level.

In this kinematically locked configuration, the spheres 22 do not require any other means to keep them in contact. In other words, no adhesive, fasteners or other means is necessary to maintain the sphere 22 in the proper position. Such extra components undesirably could impact the actual position of the spheres 22, or impede visualization of the spheres 22 under the x-rays.

Figure 6:
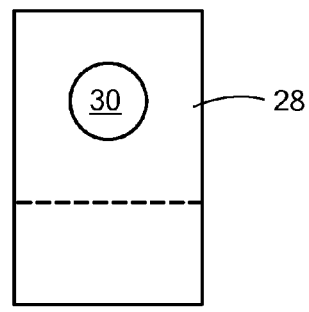
FIG. 6 schematically shows an end retaining portion of the gauge shown in FIG. 2.

FIG. 6 schematically shows a plan view of the end cap 28, which may be used with illustrative embodiments of the invention to at least in part secure the spheres 22 on the base 20. As shown in this and other figures and discussed above, the end cap 28 has a spacer 30, such as a rod or shaft with a tip, for precisely constraining, with a hard-stop, one of the ending spheres 22 (i.e., a sphere that has only one neighboring sphere). Likewise, a similar end cap 28 providing a soft-stop is added to the other side of the row of spheres for providing a minimal preload necessary to keep all of the spheres 22 in contact with each other, thus spacing the spheres 22. This preload should effectively produce a force vector in a direction that ideally is along the line formed by the centers of the spheres 22.

Figure 7:
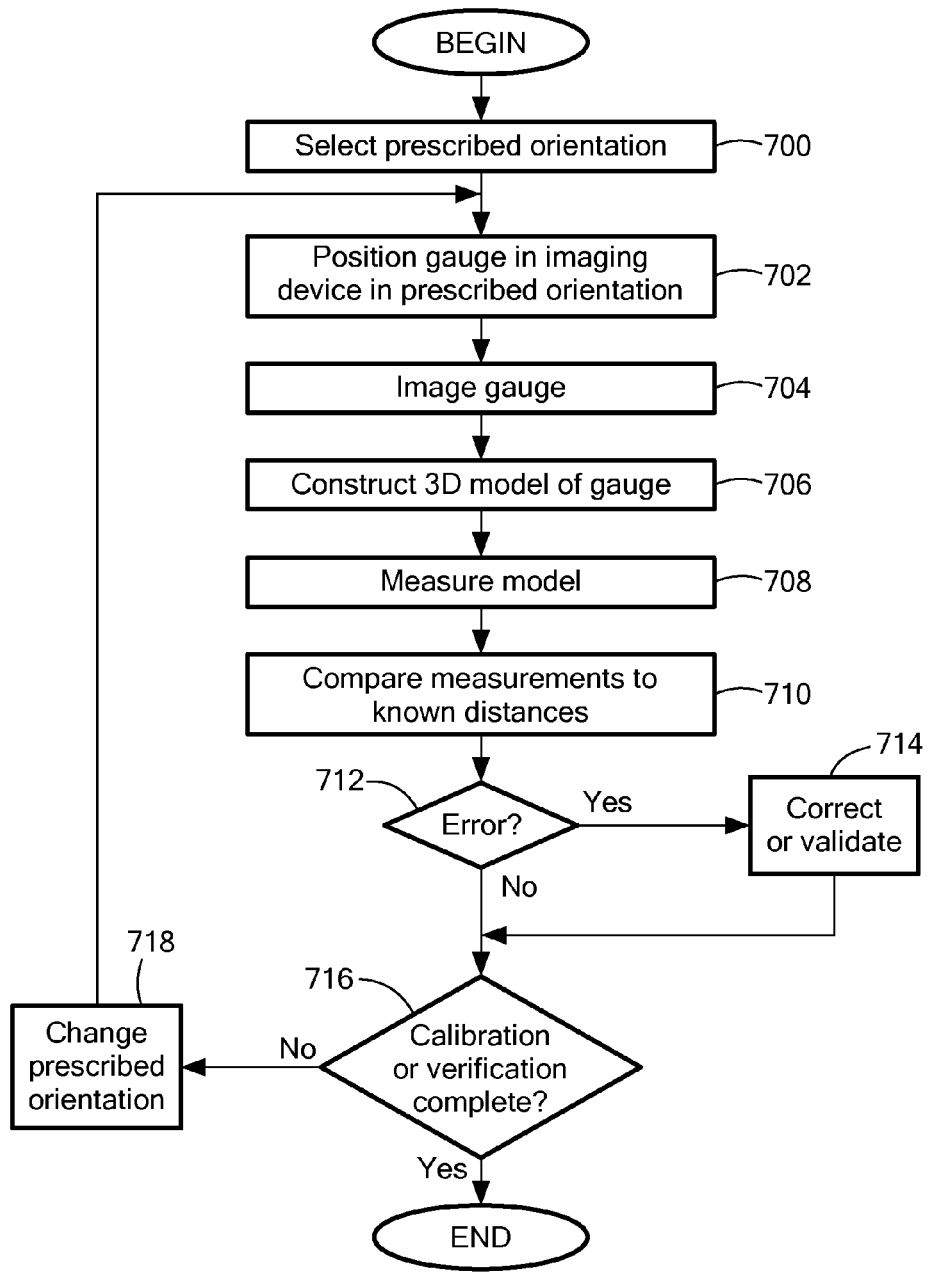
FIG. 7 shows a process of using the gauge of FIG. 2 in the x-ray computed tomography device of FIG. 1.

FIG. 7 shows a process of using the gauge 18 in accordance with one embodiment of the invention. The process begins at step 700 by selecting a prescribed orientation for the gauge 18 within the x-ray computed tomography machine 10. Next, the process physically positions the gauge 18 within the x-ray computed tomography machine 10 in the prescribed orientation (step 702) and images the gauge 18 (step 704). To that end, the gauge 18 may be positioned on the rotary stage 53 that preferably rotates the gauge 18 a full 360 degrees. During this time, the x-ray computed tomography machine 10 is taking sequenced images/projections of the gauge 18 for subsequent processing.

After the x-ray computed tomography machine 10 finishes imaging the gauge 18, the process constructs a three-dimensional model ("3D model") of the gauge 18 (step 706). A model engine (or model building module) thus uses the data from the successive images to construct the 3D model—a gauge reconstruction, which can be stored in memory. Although not necessary, rendering software may render the 3D model, and then rotate or otherwise move the ultimate 3D model for a viewer, thus showing the details of the gauge 18.

Step 708 then measures the 3D model elements to determine if it is dimensionally accurate. To that end, the process measures between preselected points within the gauge reconstruction. For example, the process may measure from the center of each sphere 22 to the center of one or more of the other spheres 22. This step thus produces a plurality of values for verification in subsequent steps.

Specifically, the actual distance between the prespecified points is known; in preferred embodiments, those distances are certified. For example, the known distance between the centers of two spheres 22 can be 10.0001 millimeters. The known distance between the centers of two other spheres 22 could be 20.0002 millimeters.

Accordingly, step 710 compares those different measured distances against the known distances and determines if there are errors (step 712). For example, the process simply may determine the difference between the various measurements and the known distances. This difference is the calibration error of the machine 10. Using the example above, if the measured distance between the first two spheres 22 (known distance 10.0001 millimeters) is 10.0004 millimeters, then the CT machine 10 has an error of 0.0003 millimeters and thus, should be appropriated adjusted.

Accordingly, if the process detects errors beyond some preset limits or tolerances (e.g., detecting this exemplary 0.0003 millimeter error), then step 714 corrects the error by refining the initial calibration settings of the machine. After correcting the errors by step 714, or if there are no errors from step 712, the process continues to step 716 to determine if calibration or verification is complete. If it is complete, then the process ends. If not complete, then the process may change the prescribed orientation of the gauge 18. For example, the prescribed orientation can be moved to be orthogonal to the initial prescribed orientation. By doing this, the operator can test various different axes within the machine.

Although the above discussion discloses various exemplary embodiments of the invention, it should be apparent that those skilled in the art can make various modifications that will achieve some of the advantages of the invention without departing from the true scope of the invention.

What is claimed is:

1. A method of calibrating or verifying the dimensional accuracy of an x-ray computed tomography machine, the method comprising:
   providing an x-ray computed tomography machine having calibration settings;
   using the x-ray computed tomography machine to image a gauge to produce a gauge reconstruction, the gauge comprising a base at least in part supporting three or more objects, each of the objects being kinematically secured on the base, each of the objects having a center, the distance between the centers of each object being known center distance values;
   measuring, in the gauge reconstruction, the distance between at least two pairs of objects to produce measured center distance values;
   comparing the measured center distance values against the known center distance values; and
   using the comparison to determine if there is a distance error in the gauge reconstruction.

2. The method as defined by claim 1 further comprising:
   modifying the calibration settings of the x-ray computed tomography machine if the comparison determines that there is a distance error in the gauge reconstruction.

3. The method as defined by claim 2 further comprising:
   determining the difference between each measured center distance value and the relevant known center distance value, modifying the calibration settings being a function of each difference.

4. The method as defined by claim 1 wherein using the x-ray comprises:
   producing a plurality of reconstructions of the gauge from a plurality of different projections, the method further comparing the measured center distance values of the objects in each of the projections against the respective known center distance values for calibrating the computed tomography machine.

5. The method as defined by claim 4 wherein measuring comprises measuring the 3D model of the gauge.

6. The method as defined by claim 1 wherein each of the objects is symmetrically shaped relative to its center point, each of the objects having an x-ray attenuation value that is greater than the x-ray attenuation value of the base.

7. The method as defined by claim 1 wherein each of the objects is substantially spherically shaped and identically sized.

8. The method as defined by claim 1 wherein the three or more objects each have a precision to at least 0.01 millimeters.

9. The method as defined by claim 1 wherein each object is kinematically locked without any external locking components between the objects.

10. The method as defined by claim 1 wherein each of the plurality of objects comprises at least one of sapphire and ruby material.

11. A method of calibrating or verifying the dimensional accuracy of an x-ray computed tomography machine, the method comprising:

using an x-ray computed tomography machine to image a gauge to produce a gauge reconstruction, the gauge comprising a base at least in part supporting three or more objects, each of the objects being kinematically secured on the base to prevent object translational movement, each of the objects having a center, the distance between the centers of each object being known center distance values;

measuring, in the gauge reconstruction, the distance between at least two pairs of objects to produce measured center distance values;

comparing the measured center distance values against the known center distance values; and using the comparison to determine if there is a distance error in the gauge reconstruction.

12. The method as defined by claim 11 wherein the gauge includes a securing member configured to apply a force to the plurality of objects, the securing member cooperating with the base to fixedly secure the plurality of objects to be substantially unmovable.

13. The method as defined by claim 11 further comprising providing the x-ray computed tomography machine.

14. The method as defined by claim 11 wherein the objects comprise first, second, and third spheres, the second sphere contacting the first and third spheres.

15. The method as defined by claim 11 wherein the at least three objects each are symmetrically shaped relative to a center point, the identifiable region of each object being the center point.

16. The method as defined by claim 11 wherein the x-ray computed tomography machine has calibration settings, the method further comprising:

modifying the calibration settings of the x-ray computed tomography machine if the comparison determines that there is a distance error in the gauge reconstruction.

17. The method as defined by claim 16 further comprising:

determining the difference between each measured center distance value and the relevant known center distance value, modifying the calibration settings being a function of each difference.

18. The method as defined by claim 11 wherein using the x-ray comprises:

producing a plurality of reconstructions of the gauge from a plurality of different projections, the method further comparing the measured center distance values of the objects in each of the projections against the respective known center distance values for calibrating the computed tomography machine.

19. The method as defined by claim 18 wherein measuring comprises measuring the 3D model of the gauge.

20. The method as defined by claim 1 wherein each of the plurality of objects is a free-standing object.

* * * * *